United States Patent [19]
Limjuco et al.

[11] 3,978,209
[45] Aug. 31, 1976

[54] ENDOTOXIN FREE MENINGOCOCCUS POLYSACCHARIDES

[75] Inventors: Guadalupe A. Limjuco, Scotch Plains; Dennis J. Carlo, South Amboy, both of N.J.

[73] Assignee: Merck & Co., Inc., Rahway, N.J.

[22] Filed: Mar. 24, 1975

[21] Appl. No.: 560,767

[52] U.S. Cl. .................................................. 424/92
[51] Int. Cl.² ........................................ A61K 39/02
[58] Field of Search .................. 424/89, 92; 195/1.5

[56] References Cited
UNITED STATES PATENTS

| | | | |
|---|---|---|---|
| 3,027,229 | 3/1962 | Towey et al. | 424/92 |
| 3,608,071 | 9/1971 | Relyveld et al. | 424/92 |

Primary Examiner—Sam Rosen
Attorney, Agent, or Firm—Donald J. Perrella; J. Jerome Behan

[57] ABSTRACT

Endotoxin contaminant in meningococcus group A and group C polysaccharide is removed by means of a phosphate containing adsorbent.

9 Claims, No Drawings

ENDOTOXIN FREE MENINGOCOCCUS POLYSACCHARIDES

BACKGROUND OF THE INVENTION

This invention relates to vaccines for immunization against group A and group C meningococcal meningitis. More particularly, it relates to a method for removing endotoxin contaminants from meningococcus group A and group C polysaccharides which are useful as vaccines.

The use as vaccines of antigenic group specific polysaccharides isolated from serologic group A and group C meningococci is known in the art and is disclosed, for example, in U.S. Pat. No. 3,636,192 to Gotschlich which disclosure is hereby incorporated by reference. A problem associated with the preparation of such vaccines, however, is the removal of endotoxin contaminant. Prior art methods resulted in significant losses of polysaccharides. For example, removal of endotoxin contaminant by ethanol treatment results in losses of polysaccharide as high as 70%.

It is, accordingly, an object of the present invention to provide an improved method for the removal of endotoxin contaminant from meningococcus group A and group C polysaccharides used as vaccine. Another object is to provide a method for removal of endotoxin contaminant which minimizes loss of polysaccharides. These and other objects of the present invention will be apparent from the following description.

SUMMARY OF THE INVENTION

Endotoxin contaminant in meningococcus group A and group C polysaccharides is removed by adsorbing the endotoxin and polysaccharides on a phosphate containing adsorbent and selectively desorbing the polysaccharides therefrom.

DETAILED DESCRIPTION

The present invention is based on the discovery that a phosphate containing adsorbent adsorbs the endotoxin contaminant more strongly than the polysaccharides and that the polysaccharides can be selectively desorbed therefrom, thereby freeing the polysaccharides from the endotoxin contaminant. Preferably, the phosphate containing adsorbent also contains calcium, e.g. calcium phosphate, apatite $[3Ca_3(PO_4)_2.CaF_2]$ or hydroxylapatite $[3Ca_3(PO_4)_2.Ca(OH_2)]$. Of these, hydroxylapatite is preferred.

According to the present invention a group A or group C polysaccharide isolated, respectively from serologic group A or group C meningococcus containing endotoxin contaminant is contacted with a calcium and phosphate containing adsorbent to adsorb both the polysaccharides and the endotoxin contaminant thereto, followed by selectively desorbing the polysaccharides from the adsorbent. The process of the present invention may be carried out in batch-wise or column operation. In batch operation, the adsorbent is equilibrated with pyrogen-free, distilled water and the group A or group C polysaccharides containing endotoxin contaminants added thereto. The mixture is mixed well and the solids separated from liquid. The solids are suspended in buffer, filtered and lyophilized. The buffer has a pH of about 7.0 and a molarity of from about 0.015 to below about 0.04, preferably about 0.025. The buffer is preferably a phosphate buffer, and most preferably a mixture of disodium hydrogen phosphate and sodium dihydrogen phosphate. The solids are subjected to replicates of this procedure to maximize recovery. Each lyophilized product is subjected to the limulus lysate assay to insure absence of endotoxin contaminant and presence of antigen activity as shown by gel diffusion. The lyophilized products may then be combined.

In column operation, the group A or group C polysaccharide containing endotoxin contaminant is dissolved in pyrogen-free, distilled water and applied to a column containing the adsorbent which column has previously been equilibrated with pyrogen-free, distilled water and washed with several bed volumes of pyrogen-free, distilled water. A linear gradient of buffer as described above, pH about 7.0, is applied from 0.0 to below about 0.4 molar. The column eluant is collected in a series of fractions and those fractions positive for hexosamine (for group A polysaccharides) or sialic acid (for group C polysaccharides) are dialyzed against pyrogen-free, distilled water and lyophilized.

The following examples illustrate the present invention without, however, limiting the same thereto. Unless otherwise indicated, all operations are conducted in the cold (4°C.).

EXAMPLE 1

25.13 mg. of meningovax group C polysaccharide containing endotoxin contaminant (prepared as described in U.S. Pat. No. 3,636,192 but omitting the final purification step) are dissolved in 5 ml. of pyrogen-free, distilled water. This solution is applied to a 17 cm × 1.3 cm column (about 23 ml. volume) of hydroxylapatite which has been previously equilibrated with pyrogen-free, distilled water. The column is next washed with several bed volumes of pyrogen-free, distilled water. A linear gradient of sodium phosphate buffer, pH 7.0 is then applied from 0.0 to 0.3 molar, each chamber containing 100 ml. of eluant. Fractions (5 ml.) are collected and individual tubes are monitored by the Warren assay for free sialic acid and the conductivity measured for each tube. Individual tubes positive for sialic acid are dialyzed against pyrogen-free, distilled water and lyophilized. The lyophilized fractions display antigen activity using gell diffusion technique and lack of endotoxin activity with the limulus lysate assay. The recovery of material from the column is 84% of the starting polysaccharide; those fractions free of endotoxin contaminant are pooled and constitute 84% of the recovered material. The overall yield of endotoxin free polysaccharides therefore is 70.56%.

EXAMPLE 2

Hydroxylapatite powder, 10.57 grams, is equilibrated with a pyrogen-free, distilled water and poured into a sterile tissue culture bottle. A sample of meningovax polysaccharide A, 67.11 mg. (prepared as described in the U.S. Pat. No. 3,636,192 but omitting the final purification step), is dissolved in 10 ml. of pyrogen-free, distilled water, poured into the tissue culture bottle and the bottle shaken overnight in the cold (4°). The solution is spun in the Sorvall centrifuge for 30 minutes at 17300 × G. The supernatant is decanted and the solids are suspended in 0.025 M sodium phosphate buffer, pH 7.0, and equilibrated overnight with shaking. The suspension is again spun for 30 minutes at 17300 × G, the supernatant decanted, and filtered through a sterile 0.45 micron filter. The solids are subjected to the foregoing procedure two more times. The combined filtrates are then dialyzed against pyrogen-free, distilled water and lyophilized. The lyophilized product displays antigen activity using gel diffusion technique and lack of endotoxin activity with the limulus lysate assay. The recovery of polysaccharide is 79% of the starting polysaccharide, 71% of the recovered polysaccharide is endotoxin free. The overall yield of endotoxin free polysaccharide therefore is 56.1%.

EXAMPLE 3

To determine the maximum capacity of the hydroxylapatite, 100 mg. of meningococcal type A polysaccharide are dissolved in 20 ml. pyrogen-free, distilled water and applied to 1 gram of the pre-swollen hydroxylapatite according to the procedure of Example 2.

Out of the 100 mg. applied to 1 gram of hydroxylapatite only about 30 mg. are adsorbed and eluted out with 0.025 sodium phosphate buffer pH 7.0. From this result, the maximum capacity of hydroxylapatite is about 30 mg. of polysaccharide per gram of hydroxylapatite.

What is claimed is:

1. A method for removing endotoxin contaminants from meningococcus group A or group C polysaccharides containing endotoxin contaminant which comprises adsorbing the polysaccharide containing endotoxin contaminant on an adsorbent selected from hydroxylapatite, calcium phosphate or apatite and selectively desorbing the polysaccharide from the adsorbent while retaining the endotoxin contaminant on the absorbent by contacting the adsorbent with a phosphate buffer having a pH of about 7.0 and a molarity below about 0.4.

2. A method according to claim 1 wherein the adsorbent is hydroxylapatite.

3. A method according to claim 1 wherein the buffer is a mixture of disodium hydrogen phosphate and sodium dihydrogen phosphate.

4. A method according to claim 1, which is carried out in batch operation.

5. A method according to claim 4 wherein the buffer has a molarity of from about 0.015 to below about 0.04.

6. A method according to claim 5 wherein the buffer has a molarity of about 0.025.

7. A method according to claim 1 which is carried out in column operation.

8. A method according to claim 7 wherein the buffer is applied in a linear gradient of from about 0.0 to below about 0.4 molar.

9. A method according to claim 7 wherein the buffer is applied in a linear gradient of from about 0.0 to about 0.3 molar.

* * * * *